United States Patent
Collier et al.

(10) Patent No.: US 10,927,060 B2
(45) Date of Patent: Feb. 23, 2021

(54) METHOD FOR THE PRODUCTION OF 2,3,3,3-TETRAFLUOROPROPENE

(71) Applicant: Arkema France, Colombes (FR)

(72) Inventors: Bertrand Collier, Montbard (FR); Dominique Deur-Bert, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/625,809

(22) PCT Filed: Jul. 16, 2018

(86) PCT No.: PCT/FR2018/051797
§ 371 (c)(1),
(2) Date: Dec. 23, 2019

(87) PCT Pub. No.: WO2019/016458
PCT Pub. Date: Jan. 24, 2019

(65) Prior Publication Data
US 2020/0131104 A1 Apr. 30, 2020

(30) Foreign Application Priority Data

Jul. 17, 2017 (FR) ...................................... 1756728

(51) Int. Cl.
*C07C 17/20* (2006.01)
(52) U.S. Cl.
CPC .................. *C07C 17/206* (2013.01)
(58) Field of Classification Search
CPC ..... C07C 17/42; C07C 17/206; C07C 17/383; C07C 21/18; C07C 17/25
See application file for complete search history.

(56) References Cited

U.S. PATENT DOCUMENTS

2009/0240090 A1   9/2009  Merkel et al.
2015/0203421 A1*  7/2015  Takahashi ............. C07C 17/206
                                                                570/160

FOREIGN PATENT DOCUMENTS

EP      3020695 A1   5/2016
WO  2012098420 A1   7/2012
WO  2013088195 A1   6/2013

OTHER PUBLICATIONS

ISA/EP; International Search Report and Written Opinion for International Patent Application No. PCT/FR2018/51797 dated Dec. 11, 2018, 10 pages.

* cited by examiner

*Primary Examiner* — Jafar F Parsa
(74) *Attorney, Agent, or Firm* — NK Patent Law

(57) ABSTRACT

The present invention relates to a process for the production of 2,3,3,3-tetrafluoropropene comprising the stages: i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane and 1,1,2,3-tetrachloropropene, in order to produce a stream B comprising 2-chloro-3,3,3-trifluoropropene, characterized in that the stream A obtained in stage i) feeds said second reactor used for stage ii); and in that stage i) is carried out at a temperature which is lower than or equal to the temperature at which stage ii) is carried out.

16 Claims, No Drawings

US 10,927,060 B2

METHOD FOR THE PRODUCTION OF 2,3,3,3-TETRAFLUOROPROPENE

CROSS-REFERENCE TO RELATED APPLICATIONS

This application is a U.S. National Stage application of International Patent Application No. PCT/FR2018/051797, filed on Jul. 16, 2018, which claims the benefit of French Patent Application No. 1756728, filed on Jul. 17, 2017.

TECHNICAL FIELD OF THE INVENTION

The present invention relates to a process for the production of fluoroolefins. In particular, the present invention relates to a process for the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds which have a structure of use as functional materials, solvents, refrigerants, inflation agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst. For example, U.S. 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2013/088195 also discloses a process for the preparation of 2,3,3,3-tetrafluoropropene from 1,1,1,2,3-pentachloropropane and/or 1,1,2,2,3-pentachloropropane, comprising the stages: (a) catalytic reaction of 1,1,1,2,3-pentachloropropane and/or 1,1,2,2,3-pentachloropropane with HF to give a reaction mixture comprising HCl, 2-chloro-3,3,3-trifluoropropene, 2,3,3,3-tetrafluoropropene, unreacted HF and optionally 1,1,1,2,2-pentafluoropropane; (b) separating the reaction mixture into a first stream comprising HCl and 2,3,3,3-tetrafluoropropene and a second stream comprising HF, 2-chloro-3,3,3-trifluoropropene and optionally 1,1,1,2,2-pentafluoropropane; (c) catalytic reaction of said second stream to give a reaction mixture comprising 2,3,3,3-tetrafluoropropene, HCl, unreacted 2-chloro-3,3,3-trifluoropropene, unreacted HF and optionally 1,1,1,2,2-pentafluoropropane; and (d) supplying the reaction mixture obtained in stage c) directly to stage a) without separation.

There is still a need for more effective processes for the production of 2,3,3,3-tetrafluoropropene

SUMMARY OF THE INVENTION

The present invention relates to a process for the production of 2,3,3,3-tetrafluoropropene comprising the stages:

i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane and 1,1,2,3-tetrachloropropene, in order to produce a stream B comprising 2-chloro-3,3,3-trifluoropropene, characterized in that the stream A obtained in stage i) feeds said second reactor used for stage ii); and in that stage i) is carried out at a temperature which is lower than or equal to the temperature at which stage ii) is carried out.

According to a preferred embodiment, stage i) is carried out at a temperature which is lower than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10'C. The temperature difference is expressed in absolute value.

Carrying out stage i) at a temperature which is lower than or equal to, preferably lower than, that at which stage ii) is carried out, in accordance with the present invention, makes it possible to reduce the formation of coke and to preserve the activity of the catalyst used in stage i). This also makes it possible to reduce the rate of formation of the side reactions, in particular the formation of the compounds HCFO-1233zdE/Z, HFO-1234zeE/Z or HFC-245fa. In addition, carrying out stage ii) at a temperature which is greater than that of stage i) makes it possible to obtain a very good selectivity for HCFO-1233xf (i.e. 2-chloro-3,3,3-trifluoropropene); in addition, the 1232xf content is maintained at a very low level. The present invention thus makes it possible to significantly improve the stability of the catalyst used in stage i) while improving the overall productivity of the process.

According to a preferred embodiment, the temperature at which stage i) is carried out and/or the temperature at which stage ii) is carried out increase(s) as these stages are carried out.

According to a preferred embodiment, the temperature at which stage ii) is carried out remains constant and the temperature at which stage i) is carried out increases as this stage is carried out.

According to a preferred embodiment, the temperature at which stage i) is carried out remains constant and the temperature at which stage ii) is carried out increases as this stage is carried out.

According to a preferred embodiment, the temperature of stage i) and/or of stage ii) is increased incrementally by 0.5° C. to 20° C., advantageously by 0.5° C. to 15° C., preferably by 0.5° C. to 10° C., more preferentially by 1° C. to 10° C., in particular by 1° C. to 8° C., more particularly by 3° C. to 8° C.

According to a preferred embodiment, stage i) is carried out at a temperature of between 330° C. and 360° C.; and the temperature of stage i) is increased incrementally by 0.5° C. to 20° C., provided that the temperature does not exceed 360° C. and that it remains lower than or equal to the temperature of stage ii).

According to a preferred embodiment, stage ii) is carried out at a temperature of 340° C. to 380° C. and the temperature of stage ii) is increased incrementally by 0.5° C. to 20° C., provided that the temperature does not exceed 380° C.

According to one embodiment, stage ii) is carried out in the presence of a catalyst at a temperature of 340° C. to 380° C. and the temperature of stage ii) is increased incrementally by 0.5° C. to 20° C.

According to a preferred embodiment, the temperature at which stage i) is carried out and the temperature at which stage ii) is carried out remain constant as these stages are carried out.

According to a preferred embodiment, stage i) and stage ii) are carried out in the presence of a catalyst, preferably a chromium-based catalyst; in particular, said catalyst is a chromium oxyfluoride or a chromium oxide or a chromium fluoride.

According to a preferred embodiment, the chromium-based catalyst also comprises a cocatalyst selected from the group consisting of Ni, Zn, Co, Mn and Mg; preferably, the content of cocatalyst is of between 0.01% and 10%, based on the total weight of the catalyst.

According to a preferred embodiment, the content by weight of 2,3-dichloro-3,3-difluoropropene (HCFO-1232xf) in the stream B is less than 1%, based on the total weight of said stream B.

DETAILED DESCRIPTION OF THE INVENTION

The present invention relates to a process for the production of 2,3,3,3-tetrafluoropropene comprising the stages:

i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane and 1,1,2,3-tetrachloropropene, in order to produce a stream B comprising 2-chloro-3,3,3-trifluoropropene.

Preferably, the stream A can also comprise 1,1,1,2,2-pentafluoropropane. Other compounds may be contained in said stream A, such as, for example, (E/Z)-1,3,3,3-tetrafluoropropene (HFO-1234ze), 1,1,1,3,3-pentafluoropropane (HFC-245fa) or (E/Z)-1233zd (1-chloro-3,3,3-trifluoropropene). The process according to the present invention is carried out under conditions effective for minimizing the content of HFO-1234ze, HFC-245fa and HCFO-1233zd in said stream A. For example, if it contains it, the content of (E/Z)-1,3,3,3-tetrafluoropropene (HFO-1234ze) can be less than 5% by weight, advantageously less than 4.5% by weight, preferably less than 4% by weight, more preferentially less than 3.5% by weight, in particular less than 3% by weight, more particularly less than 2% by weight, based on the total weight of said stream A. If it contains it, the content of 1,1,1,3,3-pentafluoropropane can be less than 8% by weight, advantageously less than 7% by weight, preferably less than 6% by weight, more preferentially less than 5% by weight, in particular less than 4% by weight, more particularly less than 3% by weight, based on the total weight of said stream A. If it contains it, the content of HCFO-1233zd (E/Z) can be less than 4% by weight, advantageously less than 3% by weight, preferably less than 2% by weight, more preferentially less than 1% by weight, in particular less than 0.8% by weight, more particularly less than 0.5% by weight, based on the total weight of said stream A.

Preferably, the process according to the invention can be carried out under effective conditions making it possible to minimize the content of 2,3-dichloro-3,3-difluoropropene (HCFO-1232xf) in the stream B. Thus, the stream B can also comprise a content of 2,3-dichloro-3,3-difluoropropene of less than 1% by weight, based on the total weight of said stream B, advantageously of less than 0.5% by weight, preferably of less than at 0.1% by weight, more preferentially of less than 0.05% by weight, in particular of less than or equal to 0.01% by weight, based on the total weight of said stream B.

Said stream B can also comprise 2,3,3,3-tetrafluoropropene and 1,1,1,2,2-pentafluoropropane.

Preferably, the stream A obtained in stage i) feeds said second reactor used for stage ii).

Preferably, stage i) is carried out at a temperature which is lower than or equal to the temperature at which stage ii) is carried out. As mentioned above, carrying out stage i) at a temperature which is lower than or equal to, preferably lower than, the temperature at which stage ii) makes it possible to reduce the formation of coke and to preserve the activity of the catalyst used in stage i) while minimizing the formation of side reactions.

According to a first preferred embodiment, the temperature at which stage i) is carried out and the temperature at which stage ii) is carried out are the same. Preferably, stage i) and stage ii) are carried out at a temperature of between 310° C. and 420° C., advantageously between 310° C. and 400° C., preferably between 310° C. and 375° C., more preferentially between 310° C. and 360° C., in particular between 330° C. and 360° C. Preferably, the temperature at which stage i) and stage ii) are carried out increases during the implementation of these stages. The temperatures can be increased, for example, when the catalyst used for stage i) is partially deactivated, that is to say when a significant decrease in the conversion is observed. In this case, the temperatures of stage i) and of stage ii) can be increased incrementally. The temperature for each of stages i) and ii) can be increased incrementally by 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6.0° C., 6.1° C., 6.2° C., 6.3° C., 6.4° C., 6.5° C., 6.6° C., 6.7° C., 6.8° C., 6.9° C., 7.0° C., 7.1° C., 7.2° C., 7.3° C., 7.4° C., 7.5° C., 7.6° C., 7.7° C., 7.8° C., 7.9° C., 8.0° C., 8.1° C., 8.2° C., 8.3° C., 8.4° C., 8.5° C., 8.6° C., 8.7° C., 8.8° C., 8.9° C., 9.0° C., 9.1° C., 9.2° C., 9.3° C., 9.4° C., 9.5° C., 9.6° C., 9.7° C., 9.8° C., 9.9° C., 10.0° C., 10.1° C., 10.2° C., 10.3° C., 10.4° C., 10.5° C., 10.6° C., 10.7° C., 10.8° C., 10.9° C., 11.0° C., 11.1° C., 11.2° C., 11.3° C., 11.4° C., 11.5° C., 11.6° C., 11.7° C., 11.8° C., 11.9° C., 12.0° C., 12.1° C., 12.2° C., 12.3° C., 12.4° C., 12.5° C., 12.6° C., 12.7° C., 12.8° C., 12.9° C., 13.0° C., 13.1° C., 13.2° C., 13.3° C., 13.4° C., 13.5° C., 13.6° C., 13.7° C., 13.8° C., 13.9° C., 14.0° C., 14.1° C., 14.2° C., 14.3° C., 14.4° C., 14.5° C., 14.6° C., 14.7° C., 14.8° C., 14.9° C., 15.0° C., 15.1° C., 15.2° C., 15.3° C., 15.4° C., 15.5° C., 15.6° C., 15.7° C., 15.8° C., 15.9° C., 16.0° C., 16.1° C., 16.2° C., 16.3° C., 16.4° C., 16.5° C., 16.6° C., 16.7° C., 16.8° C., 16.9° C., 17.0° C., 17.1° C., 17.2° C., 17.3° C., 17.4° C., 17.5° C., 17.6° C., 17.7° C., 17.8° C., 17.9° C., 18.0° C., 18.1° C., 18.2° C., 18.3° C., 18.4° C., 18.5° C., 18.6° C., 18.7° C., 18.8° C., 18.9° C., 19.0° C., 19.1° C., 19.2° C., 19.3° C., 19.4° C., 19.5° C., 19.6° C., 19.7° C., 19.8° C., 19.9° C. or 20.0° C.

The temperature can be maintained at a certain temperature for a period of time of 1 h to 5000 h before again incrementally increasing.

Preferably, the temperatures of stage i) and of stage ii) can be increased incrementally by 0.5° C. to 20° C., by 0.5° C. to 19° C., by 0.5° C. to 18° C., by 0.5° C. to 17° C., by 0.5° C. to 16° C. or by 0.5° C. to 15° C. Advantageously, the temperatures of stage i) and of stage ii) can be increased incrementally by 0.5° C. to 14° C., by 0.5° C. to 13° C., by 0.5° C. to 12° C., by 0.5° C. to 11° C. or by 0.5° C. to 10° C. Preferably, the temperatures of stage i) and of stage ii) can be increased incrementally by 0.6° C. to 10° C., by 0.7° C. to 10° C., by 0.8° C. to 10° C., by 0.9° C. to 10° C. or by 1° C. to 10° C. More preferentially, the temperatures of stage i) and of stage ii) can be increased incrementally by 1° C. to 9° C. or by 1° C. to 8° C. In particular, the temperatures of stage i) and of stage ii) can be increased incrementally by 2° C. to 8° C. or by 3° C. to 8° C.

The temperature of stage i) and of stage ii) is increased as described above while keeping these the same.

In an alternative embodiment, the temperature of stage ii) can increase more rapidly than the temperature of stage i). The temperature of stage i) is then lower than that of stage ii). This alternative embodiment then corresponds to the second preferred embodiment described above.

According to a second preferred embodiment, stage i) is carried out at a temperature which is lower than the temperature at which stage ii) is carried out.

Preferably, the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C. Preferably, the difference between the temperature at which stage i) is carried out and the temperature at which stage ii) is carried out is less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C. In a specific embodiment, the difference between the temperature at which stage i) is carried out and the temperature at which stage ii) is carried out is of between 5° C. and 20° C.

According to a preferred embodiment, the temperature at which stage i) is carried out and/or the temperature at which stage ii) is carried out increase(s) as these stages are carried out.

According to a preferred embodiment, stage i) is carried out at a temperature of between 310° C. and 420° C., advantageously between 310° C. and 400° C., preferably between 310° C. and 375° C., more preferentially between 310° C. and 360° C., in particular between 330° C. and 360° C.

According to a preferred embodiment, the temperature at which stage i) is carried out does not exceed 420° C., advantageously does not exceed 400° C., preferably does not exceed 375° C., more preferentially does not exceed 360° C.

Preferably, the temperature of stage i) can be increased incrementally when said catalyst is partially deactivated, as explained with the first embodiment.

According to a preferred embodiment, the temperature of stage i) is increased incrementally by 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6.0° C., 6.1° C., 6.2° C., 6.3° C., 6.4° C., 6.5° C., 6.6° C., 6.7° C., 6.8° C., 6.9° C., 7.0° C., 7.1° C., 7.2° C., 7.3° C., 7.4° C., 7.5° C., 7.6° C., 7.7° C., 7.8° C., 7.9° C., 8.0° C., 8.1° C., 8.2° C., 8.3° C., 8.4° C., 8.5° C., 8.6° C., 8.7° C., 8.8° C., 8.9° C., 9.0° C., 9.1° C., 9.2° C., 9.3° C., 9.4° C., 9.5° C., 9.6° C., 9.7° C., 9.8° C., 9.9° C., 10.0° C., 10.1° C., 10.2° C., 10.3° C., 10.4° C., 10.5° C., 10.6° C., 10.7° C., 10.8° C., 10.9° C., 11.0° C., 11.1° C., 11.2° C., 11.3° C., 11.4° C., 11.5° C., 11.6° C., 11.7° C., 11.8° C., 11.9° C., 12.0° C., 12.1° C., 12.2° C., 12.3° C., 12.4° C., 12.5° C., 12.6° C., 12.7° C., 12.8° C., 12.9° C., 13.0° C., 13.1° C., 13.2° C., 13.3° C., 13.4° C., 13.5° C., 13.6° C., 13.7° C., 13.8° C., 13.9° C., 14.0° C., 14.1° C., 14.2° C., 14.3° C., 14.4° C., 14.5° C., 14.6° C., 14.7° C., 14.8° C., 14.9° C., 15.0° C., 15.1° C., 15.2° C., 15.3° C., 15.4° C., 15.5° C., 15.6° C., 15.7° C., 15.8° C., 15.9° C., 16.0° C., 16.1° C., 16.2° C., 16.3° C., 16.4° C., 16.5° C., 16.6° C., 16.7° C., 16.8° C., 16.9° C., 17.0° C., 17.1° C., 17.2° C., 17.3° C., 17.4° C., 17.5° C., 17.6° C., 17.7° C., 17.8° C., 17.9° C., 18.0° C., 18.1° C., 18.2° C., 18.3° C., 18.4° C., 18.5° C., 18.6° C., 18.7° C., 18.8° C., 18.9° C., 19.0° C., 19.1° C., 19.2° C., 19.3° C., 19.4° C., 19.5° C., 19.6° C., 19.7° C., 19.8° C., 19.9° C. or 20.0° C.

According to a preferred embodiment, the temperature of stage i) is increased incrementally by 0.5° C. to 20° C., by 0.5° C. to 19° C., by 0.5° C. to 18° C., by 0.5° C. to 17° C., by 0.5° C. to 16° C. or by 0.5° C. to 15° C. Advantageously, the temperature of stage i) is increased incrementally by 0.5° C. to 14° C., by 0.5° C. to 13° C., by 0.5° C. to 12° C., by 0.5° C. to 11° C. or by 0.5° C. to 10° C. Preferably, the temperature of stage i) is increased incrementally by 0.6° C. to 10° C., by 0.7° C. to 10° C., by 0.8° C. to 10° C., by 0.9° C. to 10° C. or by 1° C. to 10° C. More preferentially, the temperature of stage i) is increased incrementally by 1° C. to 9° C. or by 1° C. to 8° C. In particular, the temperature of stage i) is increased incrementally by 2° C. to 8° C. or by 3° C. to 8° C.

In this second preferred embodiment, even if the temperature of stage i) is increased, it remains lower than the temperature of stage ii).

According to a preferred embodiment, stage ii) is carried out at a temperature of between 320° C. and 440° C., advantageously between 320° C. and 420° C., preferably between 330° C. and 400° C., more preferentially between 330° C. and 390° C., in particular between 340° C. and 380° C.

According to a preferred embodiment, the temperature at which stage ii) is carried out does not exceed 440° C., advantageously does not exceed 420° C., preferably does not exceed 400° C., more preferentially does not exceed 390° C., in particular does not exceed 380° C.

Preferably, the temperature of stage ii) is increased incrementally.

According to a preferred embodiment, the temperature of stage ii) is increased incrementally by 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2°

C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6.0° C., 6.1° C., 6.2° C., 6.3° C., 6.4° C., 6.5° C., 6.6° C., 6.7° C., 6.8° C., 6.9° C., 7.0° C., 7.1° C., 7.2° C., 7.3° C., 7.4° C., 7.5° C., 7.6° C., 7.7° C., 7.8° C., 7.9° C., 8.0° C., 8.1° C., 8.2° C., 8.3° C., 8.4° C., 8.5° C., 8.6° C., 8.7° C., 8.8° C., 8.9° C., 9.0° C., 9.1° C., 9.2° C., 9.3° C., 9.4° C., 9.5° C., 9.6° C., 9.7° C., 9.8° C., 9.9° C., 10.0° C., 10.1° C., 10.2° C., 10.3° C., 10.4° C., 10.5° C., 10.6° C., 10.7° C., 10.8° C., 10.9° C., 11.0° C., 11.1° C., 11.2° C., 11.3° C., 11.4° C., 11.5° C., 11.6° C., 11.7° C., 11.8° C., 11.9° C., 12.0° C., 12.1° C., 12.2° C., 12.3° C., 12.4° C., 12.5° C., 12.6° C., 12.7° C., 12.8° C., 12.9° C., 13.0° C., 13.1° C., 13.2° C., 13.3° C., 13.4° C., 13.5° C., 13.6° C., 13.7° C., 13.8° C., 13.9° C., 14.0° C., 14.1° C., 14.2° C., 14.3° C., 14.4° C., 14.5° C., 14.6° C., 14.7° C., 14.8° C., 14.9° C., 15.0° C., 15.1° C., 15.2° C., 15.3° C., 15.4° C., 15.5° C., 15.6° C., 15.7° C., 15.8° C., 15.9° C., 16.0° C., 16.1° C., 16.2° C., 16.3° C., 16.4° C., 16.5° C., 16.6° C., 16.7° C., 16.8° C., 16.9° C., 17.0° C., 17.1° C., 17.2° C., 17.3° C., 17.4° C., 17.5° C., 17.6° C., 17.7° C., 17.8° C., 17.9° C., 18.0° C., 18.1° C., 18.2° C., 18.3° C., 18.4° C., 18.5° C., 18.6° C., 18.7° C., 18.8° C., 18.9° C., 19.0° C., 19.1° C., 19.2° C., 19.3° C., 19.4° C., 19.5° C., 19.6° C., 19.7° C., 19.8° C., 19.9° C. or 20.0° C.

According to a preferred embodiment, the temperature of stage ii) is increased incrementally by 0.5° C. to 20° C., by 0.5° C. to 19° C., by 0.5° C. to 18° C., by 0.5° C. to 17° C., by 0.5° C. to 16° C. or by 0.5° C. to 15° C. Advantageously, the temperature of stage ii) is increased incrementally by 0.5° C. to 14° C., by 0.5° C. to 13° C., by 0.5° C. to 12° C., by 0.5° C. to 11° C. or by 0.5° C. to 10° C. Preferably, the temperature of stage ii) is increased incrementally by 0.6° C. to 10° C., by 0.7° C. to 10° C., by 0.8° C. to 10° C., by 0.9° C. to 10° C. or by 1° C. to 10° C. More preferentially, the temperature of stage ii) is increased incrementally by 1° C. to 9° C. or by 1° C. to 8° C. In particular, the temperature of stage ii) is increased incrementally by 2° C. to 8° C. or by 3° C. to 8° C.

In particular, stage ii) is carried out in the presence of a catalyst. More particularly, when stage ii) is carried out in the presence of a catalyst and when the latter is partially deactivated, the temperature of stage ii) is increased incrementally as mentioned above. The temperature can also be increased incrementally even in the absence of catalyst, for example in order to promote the selectivity of the reaction or to increase the conversion of the latter.

When the temperature of stage i) is lower than the temperature of stage ii), several configurations are possible.

According to a first configuration, the temperature of stage i) and the temperature of stage ii) remain constant as said stages i) and ii) are carried out. Thus, said first and second reactors are therefore operated with a fixed temperature difference.

According to a second configuration, the temperature of stage i) increases as it is carried out, for example in order to compensate for the loss of activity of the catalyst, while the temperature of stage ii) remains fixed as it is carried out. Thus, the temperature difference between said first and second reactors decreases as stages i) and ii) are carried out. Nevertheless, the temperature of stage i) remains lower than that of stage ii).

According to a third configuration, the temperature of stage i) and the temperature of stage ii) increase as the stages are carried out, for example incrementally as mentioned above. Thus, the temperature difference between said first and second reactors decreases, increases or remains fixed as stages i) and ii) are carried out.

According to a fourth configuration, the temperature of stage ii) increases as it is carried out, while the temperature of stage i) remains fixed as it is carried out. Thus, the temperature difference between said first and second reactors increases as stages i) and ii) are carried out.

According to a preferred embodiment, stage i) and stage ii) are carried out in the presence of a catalyst, preferably a chromium-based catalyst. Preferably, the chromium-based catalyst can be a chromium oxide (for example $CrO_2$, $CrO_3$ or $Cr_2O_3$), a chromium oxyfluoride or a chromium fluoride (for example $CrF_3$) or a mixture of these. The chromium oxyfluoride can contain a fluorine content of between 1% and 60% by weight, based on the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight, of fluorine, based on the total weight of the chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1% and 10% by weight, based on the total weight of the catalyst. The catalyst can be supported or not. A support, such as alumina, for example in its a form, activated alumina, aluminum halides ($AlF_3$, for example), aluminum oxyhalides, activated carbon, magnesium fluoride or graphite, can be used.

Preferably, the catalyst can a specific surface between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to a preferred embodiment, stage i) is carried out at atmospheric pressure or at a pressure greater than atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara. Preferably, stage i) is carried out at a pressure of between atmospheric pressure and 20 bara, preferably between 2 and 18 bara, more preferentially between 3 and 15 bara. Preferably, stage i) of the present process is carried out with a contact time between 1 and 100 s, preferably between 2 and 75 s, in particular between 3 and 50 s. Preferably, the HF/1233xf molar ratio can vary between 1:1 and 150:1, preferably between 2:1 and 125:1, more preferentially between 3:1 and 100:1. An oxidant, such as oxygen or chlorine, can be added during stage i). The molar ratio of the oxidant to the hydrocarbon compound can be between 0.005 and 2, preferably between 0.01 and 1.5. The oxidant can be pure oxygen, air, or a mixture of oxygen and nitrogen.

According to a preferred embodiment, stage ii) is carried out at atmospheric pressure or at a pressure greater than atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara. Preferably, stage ii) is carried out at a pressure of between atmospheric pressure and 20 bara, preferably between 2 and 18 bara, more preferentially between 3 and 15 bara. Preferably, stage ii) of the present process is carried out with a contact time between 1 and 100 s, preferably between 2 and 75 s, in particular between 3 and 50 s. Preferably, the HF/chlorinated compound molar ratio can vary between 1:1 and 150:1, preferably between 2:1 and 125:1, more preferentially between 3:1 and 100:1. An oxidant, such as oxygen or chlorine, can be added during stage ii). The molar ratio of the oxidant to the hydrocarbon compound can be between 0.005 and 2, preferably between 0.01 and 1.5. The oxidant can be pure oxygen, air or a mixture of oxygen and nitrogen.

Preferably, the stream A resulting from stage i) feeds the second reactor without being purified prior to its injection into the latter. Preferably, said second reactor is also fed with a stream of hydrofluoric acid and of 1,1,1,2,3-pentachloropropane or 2,3-dichloro-1,1,1-trifluoropropane or 1,1,2,3-tetrachloropropene.

Preferably, said process also comprises a stage iii) of separation of the stream B resulting from stage ii). Stage iii) makes it possible to separate the different constituents of the stream B. For example, stage iii) can make it possible to separate the 2-chloro-3,3,3-trifluoropropene from the 2,3,3,3-tetrafluoropropene and from the 1,1,1,2,2-pentafluoropropane.

EXAMPLES

Example 1

The fluorination of HCFO-1233xf to give HFO-1234yf (2,3,3,3-tetrafluoropropene) and optionally to give 1,1,1,2,2-pentafluoropropane is carried out in a first multitubular reactor with a certain degree of conversion. The stream of products which results from this fluorination feeds a second reactor. Said second reactor is also fed with a flow of hydrofluoric acid and of 1,1,1,2,3-pentachloropropane. The fluorination of HCC-240db to give HCFO-1233xf (2-chloro-3,3,3-trifluoropropene) is carried out in the second multitubular reactor with a certain degree of conversion. A recycling loop, the flow rate of which is controlled, makes it possible to return certain products to the first reactor. The first and the second reactor contain a bulk catalyst based on chromium oxide. The catalyst is activated by a series of stages comprising drying, fluorination, treatment under air and fluorination with recycling. This multistage treatment makes it possible to render the catalytic solid active and selective.

In the first reactor, the fluorination process is carried out according to the following operating conditions:
- an absolute pressure in the fluorination reactor of 6 bar absolute
- a molar ratio of the HF to the sum of the organic materials fed by the recycling loop of between 11 and 13
- a contact time of between 18 and 20 seconds
- a constant temperature in the reactor of 350° C.

In the second reactor, the fluorination process is carried out according to the following operating conditions:
- an absolute pressure in the fluorination reactor of 6 bar absolute
- a molar ratio of the HF to the sum of the organic materials fed by the recycling loop of between 11 and 13
- a contact time of between 11 and 13 seconds
- a constant temperature in the reactor of 350° C.

A final degree of conversion of 48% is achieved after 530 h of operation.

Example 2

The process according to the invention is carried out in the same way as in example 1. The operating conditions in the second reactor are identical to those of example 1. The operating conditions in the first reactor are identical to those of example 1, with the exception of the temperature:
the starting temperature in the first reactor is 330° C. and then it is gradually increased incrementally by 5° C.:
at time t=150 h, the temperature of the reactor is set at 335° C.,
at time t=320 h, the temperature of the reactor is set at 340° C.,
at time t=450 h, the temperature of the reactor is set at 345° C.

A final degree of conversion of 48% is achieved after 600 h of operation, i.e. a gain of 13%.

Example 3

The process according to the invention is carried out in the same way as in example 1. The operating conditions in the first reactor are identical to those of example 1, with the exception of the temperature in the first reactor, which is set at 340° C. A final degree of conversion of 48% is achieved after 650 h of operation, i.e. a gain of 20%.

The contents of 1233zdE/Z, 1234zeE/Z and 245fa in the stream A after 200 h of reaction are described in detail in table 1 below for the examples above. In addition, the content by weight of HCFO-1232xf in the stream B for the three examples above is 0.008 wt %, 0.01 wt % and 0.01 wt % respectively.

TABLE 1

| Content by weight in the stream A (%) | Ex. 1 | Ex. 2 | Ex. 3 |
|---|---|---|---|
| 1233zdE/Z | 0.9 | 0.6 | 0.7 |
| 1234zeE/Z | 1.5 | 0.8 | 0.9 |
| 245fa | 2.0 | 1.7 | 1.8 |
| Total | 4.4 | 3.1 | 3.4 |

The invention claimed is:

1. A process for the production of 2,3,3,3-tetrafluoropropene comprising the stages:
   i. in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and
   ii. in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane and 1,1,2,3-tetrachloropropene, in order to produce a stream B comprising 2-chloro-3,3,3-trifluoropropene,
   wherein the stream A obtained in stage i) feeds said second reactor used for stage ii); and stage i) is carried out at a temperature which is lower than or equal to the temperature at which stage ii) is carried out.

2. The process as claimed in claim 1, wherein stage i) is carried out at a temperature which is lower than the temperature at which stage ii) is carried out; and the difference between the temperature at which stage i) is carried out and the temperature at which stage ii) is carried out is greater than 0.2° C.

3. The process as claimed in claim 1, wherein the temperature at which stage i) is carried out and/or the temperature at which stage ii) is carried out increase(s) as these stages are carried out.

4. The process as claimed in claim 1, wherein the temperature at which stage ii) is carried out remains constant and the temperature at which stage i) is carried out increases as this stage is carried out.

5. The process as claimed in claim 1, wherein the temperature at which stage i) is carried out remains constant and the temperature at which stage ii) is carried out increases as this stage is carried out.

6. The process as claimed in claim 1, wherein the temperature of stage i) and/or of stage ii) is increased incrementally by 0.5° C. to 20° C.

7. The process as claimed in claim 1, wherein stage i) is carried out at a temperature of between 330° C. and 360° C.; and the temperature of stage i) is increased incrementally by 0.5° C. to 20° C., provided that the temperature does not exceed 360° C. and that it remains lower than or equal to the temperature of stage ii).

8. The process as claimed in claim 1, wherein stage ii) is carried out at a temperature of 340° C. to 380° C. and the temperature of stage ii) is increased incrementally by 0.5° C. to 20° C., provided that the temperature does not exceed 380° C.

9. The process as claimed in claim 1, wherein stage ii) is carried out in the presence of a catalyst at a temperature of 340° C. to 380° C. and the temperature of stage ii) is increased incrementally by 0.5° C. to 20° C.

10. The process as claimed in claim 1, wherein the temperature at which stage i) is carried out and the temperature at which stage ii) is carried out remain constant as these stages are carried out.

11. The process as claimed in claim 1, wherein stage i) and stage ii) are carried out in the presence of a catalyst.

12. The process as claimed in claim 1, wherein the catalyst is a chromium based catalyst that also comprises a cocatalyst selected from the group consisting of Ni, Zn, Co, Mn and Mg.

13. The process as claimed in claim 1, wherein the content by weight of 2,3-dichloro-3,3-difluoropropene (HCFO-1232xf) in the stream B is less than 1%, based on the total weight of said stream B.

14. The process of claim 2, wherein the difference between the temperature at which stage i) is carried out and the temperature at which stage ii) is carried out is greater than 1° C.

15. The process of claim 6, wherein the temperature of stage i) and/or of stage ii) is increased incrementally by 0.5° C. to 10° C.

16. The process of claim 11, wherein stage i) and stage ii) are carried out in the presence of a chromium-based catalyst.

* * * * *